United States Patent [19]

Parker

[11] 4,265,250

[45] May 5, 1981

[54] ELECTRODE

[75] Inventor: Dawood Parker, El Toro, Calif.

[73] Assignee: Battle Research and Development Associates, Cambridge, Mass.

[21] Appl. No.: 59,643

[22] Filed: Jul. 23, 1979

[51] Int. Cl.³ .............................................. A61B 5/00
[52] U.S. Cl. ................................ 128/635; 204/195 B;
204/195 P
[58] Field of Search .................... 128/635; 204/195 B,
204/195 P

[56] References Cited

U.S. PATENT DOCUMENTS

| 3,468,781 | 9/1969 | Lucero | 204/195 P |
| 3,509,034 | 4/1970 | Paine | 204/195 P |
| 3,659,586 | 5/1972 | Johns et al. | 128/635 |
| 3,700,578 | 10/1972 | Clifton et al. | 204/195 P |
| 3,700,579 | 10/1972 | Clifton et al. | 204/195 P |
| 3,878,830 | 4/1975 | Bicher | 128/635 |
| 3,912,614 | 10/1975 | Spracklen et al. | 128/635 X |
| 3,998,212 | 12/1976 | Reichenberger | 128/635 |
| 4,148,305 | 4/1979 | Reichenberger | 128/635 |
| 4,185,620 | 1/1980 | Hagihara | 128/635 |

FOREIGN PATENT DOCUMENTS 2003275 3/1979 United Kingdom ..................... 128/635

OTHER PUBLICATIONS

Scacci et al, "O₂ Tension Monitoring", Med. Inst., vol. 10, No. 4, pp. 192-194, Jul.-Aug. 1976.
Vesterager, "Continuous Trans. Meas. . . PO₂", Measurement of $O_2$, 1976, pp. 260-270.

Primary Examiner—Lee S. Cohen

[57] ABSTRACT

An electrode for measuring gas concentration in blood and having a disposable, skin-contact assembly installed in a reusable base; the disposable assembly includes an anode, cathode, electrolyte, and membrane, and the base includes a heater and means for conducting heat and electrical current to the disposable assembly.

10 Claims, 3 Drawing Figures ized lv# ELECTRODE

FIELD OF THE INVENTION

This invention relates to electrodes for measuring gas concentration in blood.

BACKGROUND OF THE INVENTION

It is often desirable to measure the oxygen content of blood without taking a blood sample (e.g., for fetal monitoring during delivery). This can be done by measuring the oxygen released through the skin from capillaries lying adjacent the skin surface, the so-called transcutaneous partial pressure of oxygen ($t_cPO_2$). Conventionally the measurement is made by adhering to the skin an electrode having a membrane permeable to oxygen. One such electrode is disclosed in Eberhard et al., "An Introduction to Cutaneous Oxygen Monitoring in the Neonate," Hoffmann-La Roche & Co., AG (1976). Oxygen passes through the membrane and into an electrolyte region. The amount of oxygen is detected by measuring the current flowing through the electrolyte between an anode and a cathode. A heater in the electrode warms the skin to stimulate release of oxygen. The anode, cathode, electrolyte region, and heater are incorporated into a reusable unit. The membrane is removed after each use to add fresh electrolyte. As it is important to maintain the elevated temperature of the electrode within a narrow temperature range to assure measurement accuracy, the electrode is temperature calibrated.

SUMMARY OF THE INVENTION

It has been found that these electrodes can be made less expensive and simpler to use by dividing the electrode into a reusable base and a disposable, skin-contact assembly. The disposable assembly includes an anode, cathode, electrolyte and membrane. The base includes a heater and means for conducting heat and electrical current to the disposable assembly. After each use, the disposable assembly is removed and a new assembly installed, a much less time consuming procedure than removing the membrane, adding electrolyte, and calibrating. The reusable base need be temperature calibrated only once, as it contains the heater.

In some preferred embodiments, the membrane is dip-coated onto the electrolyte region by applying a solution of the membrane dissolved in a solvent and allowing it to harden; in use the membrane is activated by applying a drop of electrolyte to the outside of the membrane and waiting for the electrolyte to penetrate; heat and electricity are conducted to the disposable assembly via its threaded connection to the base and an annular metallic (e.g., silver) member forming the anode; the cathode is a rod (e.g., platinum) mounted within and insulated (e.g., by a glass annulus) from the annular anode; electrical current reaches the cathode via a resilient contact in the base; the membrane is polyhydroxyethylmethacrylate; and temperature sensors (e.g., thermistors) are provided in the base for controlling the heater and for signalling an alarm if an unsafe temperature is reached. The dip coating provides very repeatable membrane characteristics, and thus permits calibration (zero offset and gain) for gas concentration to be done initially and not repeated for each new disposable assembly.

In other preferred embodiments, a coating of dry electrolyte salt is applied before the membrane coating, and the electrode is activated by applying a drop of water.

PREFERRED EMBODIMENTS

The structure and operation of preferred embodiments of the invention will now be described.

DRAWING

STRUCTURE

Figure 1:
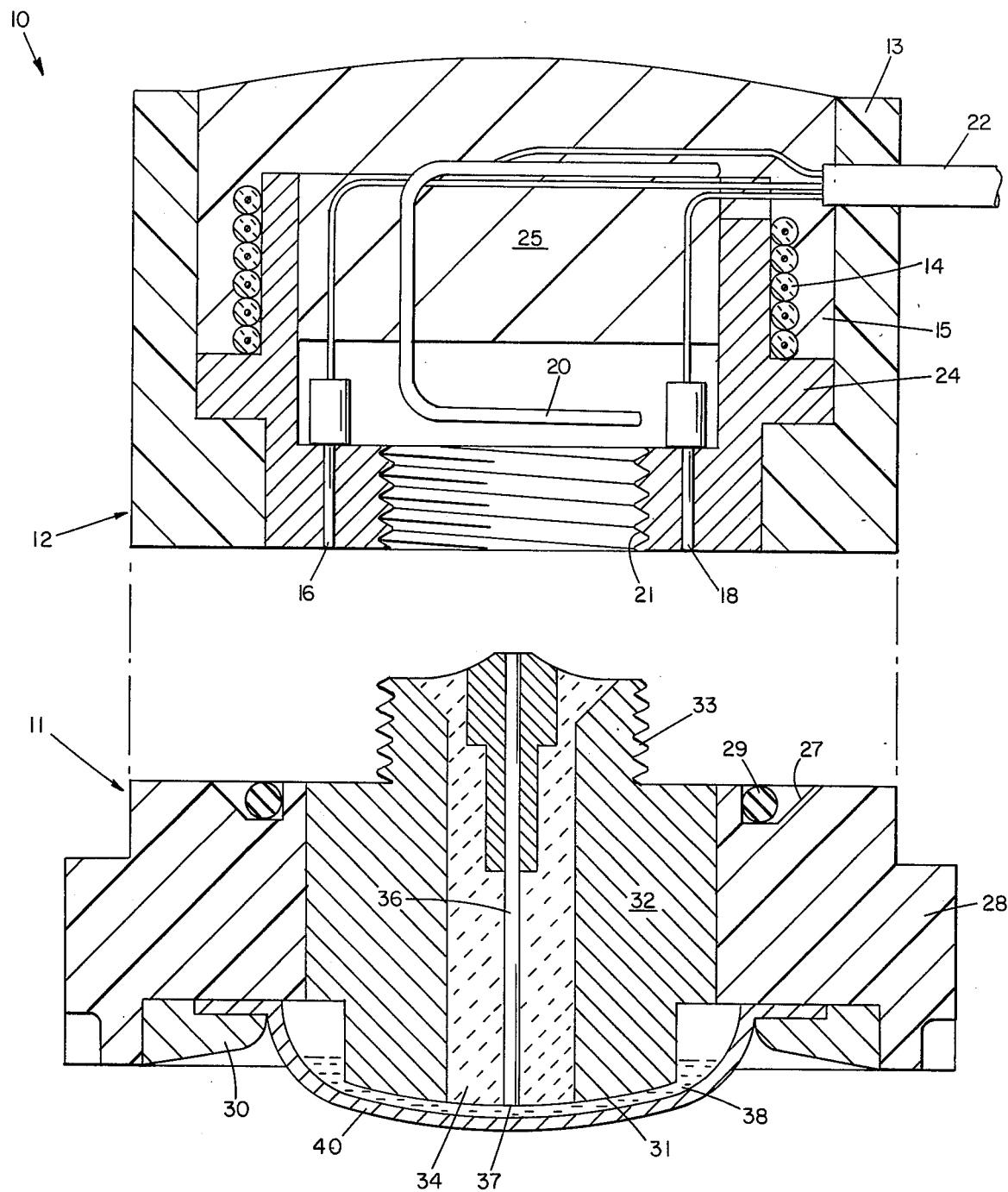
FIG. 1 is a somewhat diagrammatic, sectional view of an electrode embodying the invention.

Referring to FIG. 1, there is shown an electrode 10 for measuring transcutaneous oxygen pressure ($t_cPO_2$). The electrode consists of reusable base 12 and disposable, skin-contact assembly 11.

Base 12 has a knurled Delrin outer cover 13 (1.5 cm diameter, 0.9 cm tall) surrounding inner body 24 of stainless steel. Heating coil 14 (copper wire, 200 ohms) is wound in annular gap 15 between cover 13 and body 24. Two thermistors 16, 18 (Fenwal type, 100 K ohms at 25° C.) are embedded in the bottom of body 24 next to female threads 21, which engage mating threads on assembly 11. A phosphor-bronze spring contact 20 extends downward in the center of the base and is supported in epoxy potting compound 25. Wires from cable 22 connect contact 20, body 24, and the thermistors 16, 18 to conventional control electronics (not shown).

Figure 2:
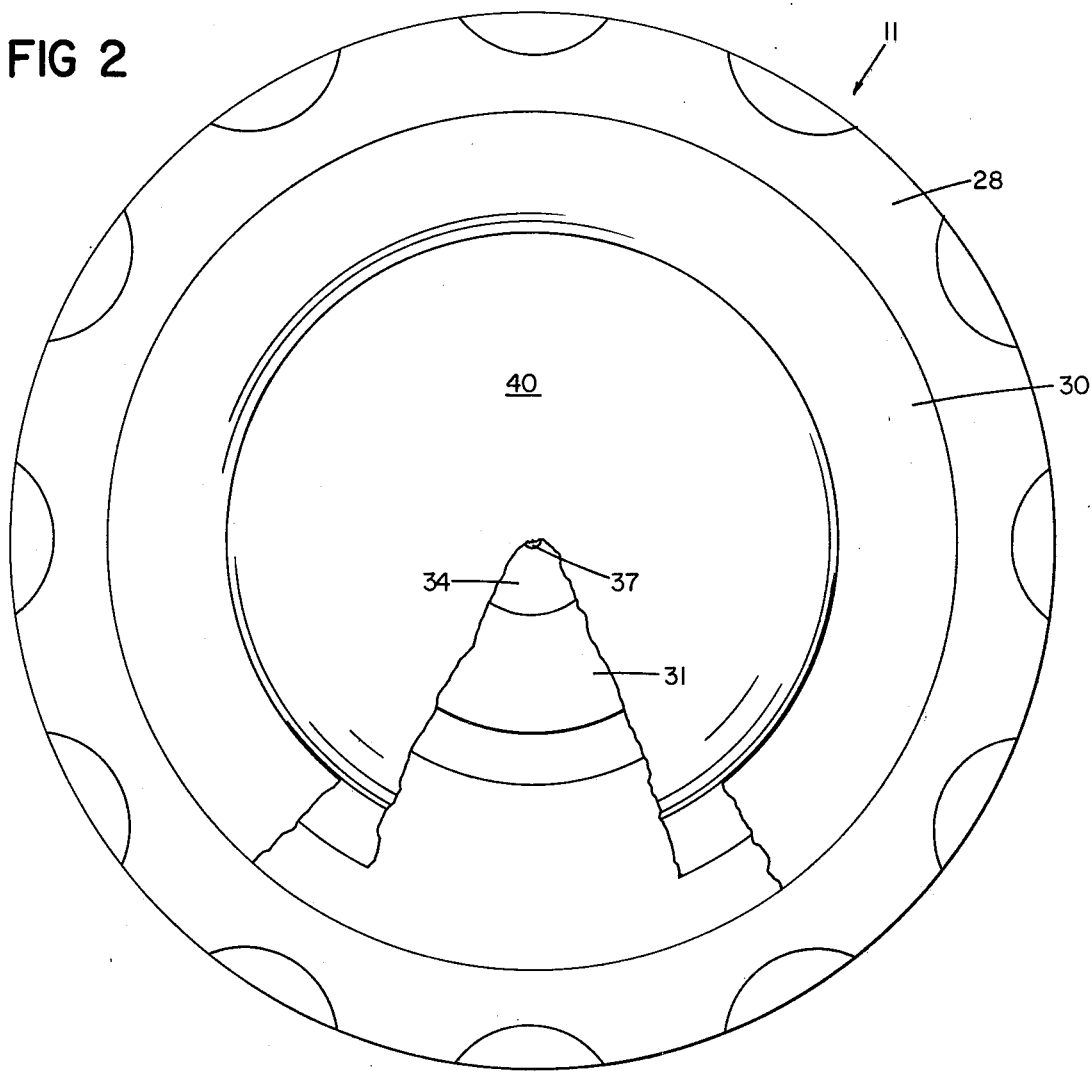
FIG. 2 is a plan view of the underside of said embodiment, showing the membrane, cathode, and anode.

Disposable assembly 11 has a knurled Delrin outer cover 28 (2.0 cm diameter) surrounding an inner silver annular member 32, the end of which forms anode 31. Cover 28 includes an annular groove 27 and O-ring seal 29, for sealing with base 12. Member 32 has male threads 33 which mate with threads 21 on the base. Member 32 is sealed with epoxy to central glass insulator 34, which in turn surrounds and is sealed with epoxy to rod 36 (25 microns in diameter), the end of which forms cathode 37. The skin-contacting base of assembly 11 is dip-coated with a solution of polyhydroxyethylmethacrylate (PHEMA) dissolved in a solvent. The solvent evaporates to leave water-vapor permeable membrane 40 (FIGS. 1 and 2). A retaining ring 30 is then bonded over the membrane to retain it.

OPERATION

The first step in use of the electrode is calibrating thermistor 16, heating coil 14, and the electronics so as to produce the desired operating temperature (either 44° C. or 45° C.). This calibration is done once for the base and need not be repeated each time a new disposable assembly is inserted.

The next step is to calibrate the electronics for the zero offset and gain relating electrical current to oxygen concentration. Either or both of these calibrations need not be repeated each time a new disposable assembly is inserted.

To make an oxygen measurement on the skin, a new assembly 11 is screwed into base 12 and activated by applying a drop of electrolyte solution (saline) on the surface of membrane 40. The solution penetrates the membrane to form an electrolyte solution 38 between the membrane and anode 32 and cathode 36. Penetration takes about 60 seconds for the PHEMA membrane.

Power is now applied to the heater coil, and the electrode is allowed to reach equilibrium temperature (44° C. or 45° C.) while suspended in air and out of contact with the skin. If an oxygen calibration is to be performed, the electronics are adjusted to make the output correspond to the partial pressure of ambient oxygen. For example, at a barometric pressure of 760 mm Hg and an electrode temperature of 44° C., the partial pressure of $O_2$ in air (which is 20.9% $O_2$) is 145 mm Hg. A further correction for the vapor pressure of water vapor is also made because in operation the electrode is continuously in contact with water on the skin.

The electrode is then adhered to the skin with an adhesive disk such as those used with EKG machines. A waiting period of about 20 minutes is required to dilate the capillaries sufficiently for release of oxygen. After measurements are complete, assembly 11 is unscrewed from base 12 and disposed of.

Temperature is maintained at the electrolyte by heat from coil 14 conducted through steel body 24 and anode 32. The output of thermistor 16 is used to switch current to coil 14 on and off to maintain anode temperature to within 0.2° C. of the desired temperature. The second thermistor 18 activates a safety alarm if an unsafe temperature is reached.

A voltage of (e.g., 800 mV) is applied between cathode 36 and anode 32. Glass insulator 34 provides a high-resistance path between anode and cathode in order to make possible measurement of the very small electrolyte current (about $1 \times 10^{-9}$ A). The excellent glass to cathode seal provided by the epoxy assures that only the tip surface of the cathode is exposed to the electrolyte. This eliminates variation in the output current due to variations in exposed cathode surface area.

OTHER EMBODIMENTS

Figure 3:
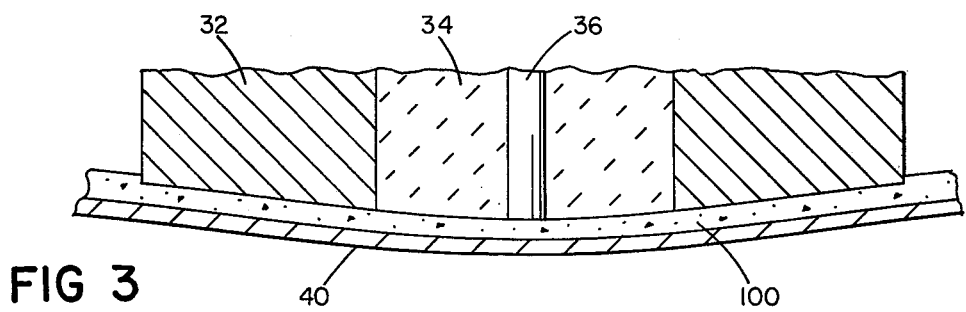
FIG. 3 is a fragmentary, sectional view of another embodiment of the invention.

Other embodiments of the invention are within the following claims. For example, a coating 100 (FIG. 3) of electrolyte salt such as KCl dispersed in methyl cellulose can be applied before the membrane coating and water substituted for the electrolyte solution as the activating liquid. In this instance the membrane need only be permeable to water vapor, and thus polyvinylchloride or polystyrene can be substituted for the polyhydroxyethylmethacrylate. These membrane materials require about 20 to 50 minutes for penetration of water vapor. One method for reducing this time is to store the disposable assemblies in humid bags.

What is claimed is:

1. Apparatus for measuring the concentration of gases in blood, comprising
   a disposable skin-contact assembly, comprising
   a first support,
   anode and cathode electrodes mounted on said support, and
   a skin-contact membrane permeable to said gases mounted on said support adjacent to said electrodes to define an electrolyte region between said membrane and said electrodes, and
   a reusable base assembly, comprising
   a second support,
   a metal member mounted on said second support,
   heat source means mounted on said second support for supplying heat through said disposable assembly to said electrolyte region,
   an electrical contact member mounted on said second support, and
   means for connecting said metal member and said contact member to an electrical cable to provide an electric potential therebetween,
   said assemblies further comprising respective interlocking means for bringing said metal member into contact with one said electrode and said contact member into contact with the other said electrode.

2. The apparatus of claim 1 wherein said heat source means comprises means to heat said metal member.

3. The apparatus of claims 1 or 2 wherein said electrode in contact with said metal member is said anode.

4. The apparatus of claim 1 wherein said interlocking means comprises threaded portions of said assemblies, respectively.

5. The apparatus of claim 1 wherein said anode is an annular member surrounding said cathode.

6. The apparatus of claim 1 further comprising a coating of dry electrolyte salt in said electrolyte region, said coating of salt being beneath said membrane, whereby said disposable assembly is activated by applying water to the outside of said membrane, the water penetrating the membrane and dissolving said salt coating to form an electrolyte solution.

7. The apparatus of claim 6 wherein said membrane comprises polyvinyl chloride or polystyrene.

8. The apparatus of claim 1 wherein said electrolyte region is free of electrolyte prior to use of said apparatus and said membrane is selected to pass water vapor and electrolyte ions, whereby said disposable assembly is activated by applying an electrolyte solution to the outside of said membrane and allowing said solution to penetrate said membrane.

9. The apparatus of claim 8 wherein said membrane comprises polyhydroxyethylmethacrylate.

10. The apparatus of claim 6 or 8 wherein said membrane is deposited on said first support over said electrodes by applying a coating of membrane material dissolved in solvent and allowing the coating to harden.

* * * * *

UNITED STATES PATENT AND TRADEMARK OFFICE
CERTIFICATE OF CORRECTION

PATENT NO. : 4,265,250

DATED : May 5, 1981

INVENTOR(S) : Dawood Parker

It is certified that error appears in the above-identified patent and that said Letters Patent are hereby corrected as shown below:

Change Assignee "Battle Research and Development Associates" to --Brattle Research and Development Associates--.

Signed and Sealed this

Fourteenth Day of July 1981

[SEAL]

Attest:

Attesting Officer

GERALD J. MOSSINGHOFF

Commissioner of Patents and Trademarks